United States Patent [19]

Eldin et al.

[11] 4,206,309
[45] Jun. 3, 1980

[54] VINYL ETHERS, PROCESS FOR THEIR PREPARATION, AND THEIR USE FOR THE PREPARATION OF POLYMERS

[75] Inventors: Sameer H. Eldin, Birsfelden; Friedrich Stockinger, Hölstein, both of Switzerland

[73] Assignee: Ciba-Geigy Corporation, Ardsley, N.Y.

[21] Appl. No.: 920,301

[22] Filed: Jun. 29, 1978

[30] Foreign Application Priority Data

Jul. 7, 1977 [CH] Switzerland ............... 8433/77

[51] Int. Cl.² ............... C07D 233/72; C07D 233/80; C07D 407/06
[52] U.S. Cl. ............... 548/309; 548/310; 548/312
[58] Field of Search ............... 548/312, 310, 309

[56] References Cited

U.S. PATENT DOCUMENTS

| | | | |
|---|---|---|---|
| 3,449,353 | 6/1969 | Porret et al. | 548/309 |
| 3,755,350 | 8/1973 | Sauli | 548/312 |
| 3,772,326 | 11/1973 | Batzer | 548/312 |
| 3,864,358 | 2/1975 | Porret et al. | 548/309 |
| 4,092,479 | 5/1978 | Parsons, Jr. et al. | 548/312 |

Primary Examiner—Alan L. Rotman
Assistant Examiner—Robert C. Whittenbaugh
Attorney, Agent, or Firm—Luther A. R. Hall

[57] ABSTRACT

The present invention relates to new hydantoin vinyl ethers of the formula

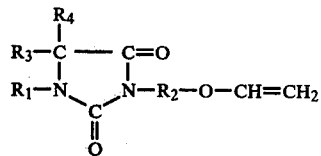

in which $R_1$ is hydrogen or an organic radical, $R_2$ is an alkylene group, and $R_3$ and $R_4$ are preferably lower alkyl groups. These compounds are used for the preparation of homopolymers and copolymers, which can used as thickeners, solubilizing agents, binders, thixotropic agents, complexing agents, stabilizers and so forth.

5 Claims, No Drawings

VINYL ETHERS, PROCESS FOR THEIR PREPARATION, AND THEIR USE FOR THE PREPARATION OF POLYMERS

The present invention relates to hydantoin vinyl ethers, to a process for their preparation and to their use for the preparation of homopolymers and copolymers.

These polymers have diverse possible uses. Depending on their physical properties they may be used as thickeners, solubilising agents, crosslinking agents, flocculating agents, dispersants, adhesives, stiffeners, binders, crystal growth regulators, pseudo-plasticisers (thixotropic agents), complexing agents, stabilisers and builders for synthetic detergents, and correspondingly they can be employed in numerous branches of industry, for example as a wet strength agent in the paper industry, as a size in the textile industry, as a thixotropic agent in the pharmaceutical, cosmetic and paints industries and as a binder in agricultural chemistry.

Agents which serve similar purposes have already been disclosed, for example in U.S. Pat. No. 3,087,853; this describes water-soluble compositions of iodine and methylcellulose or carboxymethylcellulose, amine-formaldehyde resins or copolymers of maleic anhydride and another vinyl compound, e.g. styrene, vinyl acetate, vinyl chloride, vinyl ethers, indene, coumarone, cinnamic acid, vinyl methyl ketone, acrolein, vinyl tetrahydronaphthalene, stilbene or acrylic acid, and their use as an antiseptic and disinfectant. Similar compositions based on copolymers of maleic anhydride and a vinyl alkyl ether are disclosed by U.S. Pat. No. 2,752,281. Compared to these compounds, the polymers based on the monomers according to the invention exhibit better solubilising properties (compare Example VI).

U.S. Pat. No. 3,197,477 describes allylhydantoins. Pharmaceutically active mercury compounds are prepared from these. Their use for the preparation of polymers is not mentioned.

U.S. Pat. No. 3,161,538 relates to the treatment of textile goods with solutions of alkali metal salts of partial esters of copolymers of maleic anhydride with a vinyl-lower alkyl ether. It was surprising that the compounds of the present invention furnish copolymers which give softer, more supple and better-adhering films on textiles.

British Pat. No. 846,601 discloses vinylhydantoins, and homopolymers, copolymers and terpolymers of these. Co-components mentioned are ethylenically unsaturated compounds, e.g. vinyl acetate, acrylonitrile, vinyltoluene and styrene.

Homopolymers of 3-alkylidenehydantoins are known from German Offenlegungsschrift No. 2,437,916. They are used as additives to polyacrylonitrile spinning solutions. The filaments obtained after spinning are distinguished by low flammability.

Finally, German Offenlegungsschrift No. 2,437,917 describes copolymers of acrylonitrile and a 3-allyl-hydantoin. These copolymers can be converted to films, sheets, fibres and filaments.

All these polymers cannot be used, or at best cannot be used as effectively, in the way in which the polymers prepared from the monomers of the invention are used.

The monomeric compounds of the invention, and the polymers prepared therefrom, are novel. They correspond to the formula I

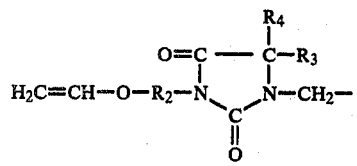

in which $R_1$ is hydrogen or an organic radical, preferably the phenyl, methyl, cyanoethyl, glycidyl, hydroxymethyl, hydroxyethyl, hydroxypropyl, acetyl, 2-hydroxy-2-phenylethyl or

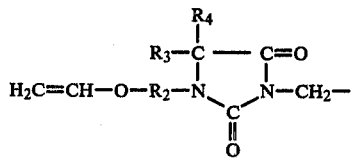

group, especially hydrogen or the methyl group, $R_2$ is an alkylene group having 1 to 6, preferably 2 to 4, carbon atoms, especially the ethyl group, or the $(-$alkylene$-O-)_n$-alkylene group, in which the alkylene group has 1 to 6 carbon atoms, especially 2 carbon atoms, and n is a number from 1 to 6, especially 1 or 2, and $R_3$ and $R_4$ independently of one another are each hydrogen or an alkyl group having 1 to 6, preferably 1 to 3, carbon atoms, especially the methyl group or an aryl group, or together are an alkylene group, preferably the tetramethylene or pentamethylene group.

According to the invention, these hydantoin vinyl ethers of the formula I are prepared by reacting a hydantoin of the formula II

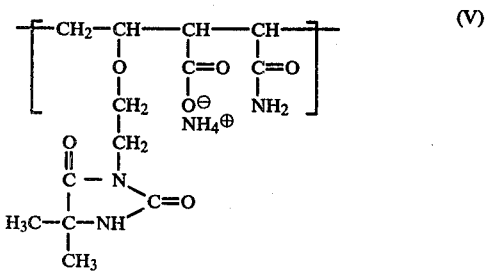

with a ω-chloroalkyl vinyl ether of the formula (III)

Cl—$R_2$—O—CH=$CH_2$     (III)

in which the groups $R_1$, $R_2$, $R_3$ and $R_4$ have the same meanings as in formula (I).

This reaction is preferably carried out in the presence of an alkaline compound, especially an alkali metal carbonate, in a solvent, especially dimethylformamide, at above 100° C.

Another process of preparation is based on the synthesis of vinyl ethers described by Robert L. Adelman in J. Am. Chem. Soc., Vol. 75, 2678 et seq. (1953). In this, an alcohol of the formula (IV)

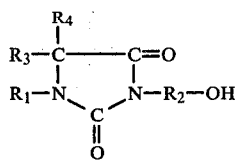

in which $R_1$, $R_2$, $R_3$ and $R_4$ have the same meanings as in formula I, is reacted with vinyl acetate in the presence of a mercury salt, such as mercury acetate, as the catalyst, at a temperature below 0° C. Preferably more than 4 mols, for example 5 to 8 mols, of vinyl acetate are employed per mol of the alcohol of the formula (IV), and the reaction is carried out without a solvent, in a heterogeneous phase, preferably at −25° to −10° C.

Further possible methods of synthesis are given, for example, in U.S. Pat. No. 1,959,927, in Houben-Weyl, Volume 14/1,924 et seq. (1961), in Industrial and Engineering Chemistry 39, 180 et seq. (1947), in Tetrahedron, Vol.28, 227–239 (1972) and in Synthesis, 736 et seq. (November 1975).

The hydantoin vinyl ethers of the invention are used as starting materials for polymers. They may be homopolymerised or may be polymerised together with one or two comonomers to give a copolymer or terpolymer respectively. The copolymers and terpolymers have excellent thickening, pseudo-plastic, complexing and adhesive properties.

The homopolymerisation is carried out at from −70° C. to +200° C., usually by warming the monomers to 50°-200 C. in an aprotic solvent, such as benzene, or in the absence of a diluent, and in the presence of a catalyst, such as iodine, silver perchlorate or triphenylmethyl chloride or above all a Friedel-Crafts catalyst such as $BF_3$ etherate. For the copolymerisation, a mixture of a compound of the formula (I) with one or two comonomers, in solution or in aqueous emulsion, is used, a catalyst being added. Suitable catalysts, which are free radical initiators, are peroxides, for example potassium peroxydisulphate or benzoyl peroxide, as well as azo compounds, for example azoisobutyronitrile, or redox initiator systems, for example a mixture of iron-III acetylacetonate, benzoin and benzoyl peroxide. Suitable solvents are, inter alia, aromatic hydrocarbons, chlorohydrocarbons and ketones, for example benzene, toluene, xylene, ethylbenzene, isopropylbenzene, ethylene chloride, propylene chloride, methylene chloride, chloroform, methyl ethyl ketone, acetone and cyclohexanone. Benzene, toluene, xylene and ethylene chloride are preferred.

Examples of suitable comonomers are other olefinically unsaturated compounds, such as vinyl acetate, acrylonitrile, vinyl ethers, diketene or derivatives of $\alpha,\beta$-unsaturated dicarboxylic acids. These comonomers are used in amounts of from 0.01 to 100 mols per mol of the hydantoin vinyl ether of the formula (I), but preferably in a molar ratio of 1:1.

Vinyl ethers to be mentioned are those of the formula (I) and alkyl vinyl ethers. Examples of derivatives of $\alpha,\beta$-unsaturated dicarboxylic acids are the anhydrides of the following acids: maleic acid, chloromaleic acid, methylmaleic acid, ethylmaleic acid, dichloromaleic acid, diphenylmaleic acid, n-butylmaleic acid, phenylmaleic acid, chloromethylmaleic acid, bromophenylmaleic acid and itaconic acid.

In addition to the derivative of an $\alpha,\beta$-unsaturated dicarboxylic acid, the copolymer can contain another vinyl component as a third constituent, for example styrene or isobutyl vinyl ether in addition to maleic anhydride, and in particular the ratios of the three constituents are 0.01–100 mols: 0.01–100 mols: 0.01–100 mols, but preferably about 1:1:1.

The copolymers obtained from these anhydrides may, depending on the end use, be worked up in the form of the free acid, of an amide/ammonium salt (i.e. derivatives in which the carboxyl groups have been partly converted to amides and partly to ammonium salts—see also formula V), a sodium, potassium, calcium or ammonium salt, a monoester or diester, the degree of esterification being from 1 to 100%, or a cyclic imide; these compounds may be obtained, for example, by adding anhydrous ammonia or sodium hydroxide, potassium hydroxide or calcium hydroxide to a suspension of the copolymer in benzene. It is also possible to filter the suspension, dry and grind the product, suspend it in water and convert it to the sodium salt by adding sodium hydroxide solution.

The amide/ammonium salt of vinyloxyethyl-5,5-dimethyl-hydantoin/maleic anhydride copolymers possesses structural units of the formula (V)

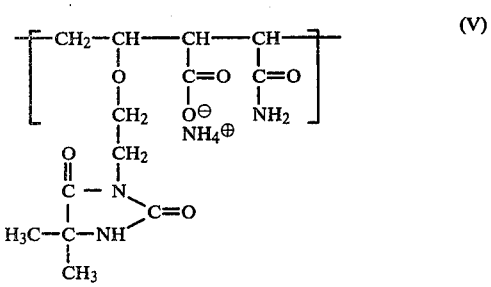

Compared to the non-saline copolymers it has the following advantages: better solubility in water at room temperature, approximately neutral aqueous solutions (pH value 6.2), a greater thickening effect, better free-flowing characteristics and reduced static charge, if any.

Diesters may be obtained from the copolymers in organic solvents by adding esterification catalysts and distilling off water at an elevated temperature. Monoesters are prepared similarly, with appropriately modified molar ratios of the reactants, and without distilling off water. These monoesters can be converted to salts by adding alkali.

The imides can be obtained by reacting amide/ammonium salts of the copolymers with acetic anhydride and anhydrous acetic acid.

The copolymer can also be crosslinked by reaction with a compound which is polyfunctional in respect of the anhydride group or of a derivative of the anhydride group. The amount of the crosslinking agent can lie within wide limits, namely from 1 to 99 mol%, relative to the acid anhydride groups or groups derived therefrom. Suitable polyfunctional compounds include epoxy resins, polyols, polyphenols, polyamines, compounds containing metal ions, polyisocyanates, polyhalides and acrylamides such as methylene-bis-acrylamide or methylene-bis-methacrylamide. The polymers can also be used in combination with plasticizers such as glycerol, sorbitol, polyethylene glycol and similar products.

EXAMPLE 1

3-[2-(Vinyloxy)-ethyl]-5,5-dimethyl-hydantoin 128.1 g (1.0 mol) of 5,5-dimethyl-hydantoin, 108.7 g (1.0 mol+2% excess) of 2-chloroethyl vinyl ether, 72.56 g (0.5 mol+5% excess) of anhydrous potassium carbonate and 300 ml of dimethylformamide are stirred in a glass flask, equipped with a stirrer, thermometer and reflux condenser, for 4 hours and 25 minutes at 126°–130° C. The reaction mixture is then filtered hot and the clear filtrate is concentrated on a rotary evaporator at 80° C. under vacuum from a waterpump. The residue is dried for 2 hours at 100° C. and 0.1 mm Hg, and 191.81 g (96.7% of theory) of a clear, brownish, viscous crude product are obtained; this is purified by distillation. 172.4 g (86.97% of theory) of a clear, yellowish, viscous distillate, boiling at 126° C./0.04 mm Hg are obtained. Refractive index $n_D^{20}=1.4872$.

Elementary analysis: calculated: 54.54% C, 7.12% H, 14.13% N; found: 54.71% C, 7.06% H, 14.32% N.

The H-NMR spectrum is in accord with the following structure:

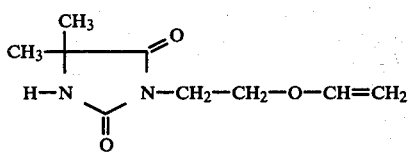

The same compound may also be obtained as follows: 0.3 g of $H_2SO_4$ is added dropwise, with vigorous stirring, to 400 ml of freshly distilled vinyl acetate, 0.002 g of Cu resinate and 0.96 g of mercury acetate, at −25° C., in a 1 liter round-bottomed flask. 41.4 g of 3-hydroxyethyl-5,5-dimethyl-hydantoin are then added, with brief stirring, under conditions such that the temperature in the flask does not rise above −20°. The resulting dispersion is kept at a temperature between −20° C. and −30° C., with slow stirring, and after 16 hours the undissolved alcohol (5.2 g) is filtered off, the solution is poured into ice water which contains sufficient sodium carbonate that the pH value resulting after addition of the solution is 8 or above, and finally the organic phase is separated from the aqueous phase, washed twice with water, dried over sodium sulphate and concentrated on a rotary evaporator. 27.4 g (=57.5% of theory) of 3-vinyloxyethyl-5,5-dimethyl-hydantoin are obtained.

EXAMPLE 2

3-[2-(Vinyloxy)-ethyl]-5-methyl-5-ethyl-hydantoin

A mixture of 71.04 g (0.5 mol) of 5-methyl-5-ethyl-hydantoin, 55.94 g (0.5 mol+5% excess) of 2-chloroethyl vinyl ether, 36.28 g (0.25 mol+5% excess) of anhydrous potassium carbonate and 150 ml of dimethylformamide is stirred, analogously to Example 1, for 4 hours and 35 minutes at 122°–129° C. After completion of the reaction, the reaction mixture is filtered and the clear filtrate is concentrated on a rotary evaporator at 80° C. under vacuum from a waterpump. The residue is taken up in 200 ml of acetone, 2 g of active charcoal are added and the mixture is kept at the boil for 15 minutes. It is then filtered and the filtrate is concentrated on a rotary evaporator at 60° C. under vacuum from a water-pump. The residue is freed from non-volatile constituents at 60° C. and 0.5 mm Hg and 86.9 g (81.9% of theory) of a yellowish, viscous crude product are obtained. This is purified by distillation in a high vacuum and 80.34 g (75.7% of theory) of the desired product, of boiling point 132° C./0.2 mm Hg, are obtained.

Elementary analysis: calculated: 56.59% C, 7.60% H, 13.20% N; found: 56.43% C, 7.77% H, 13.06% N.

The H-NMR spectrum is reconcilable with the following structure:

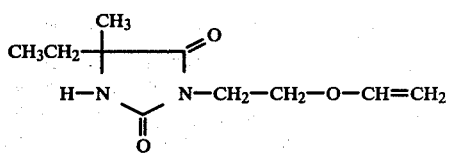

EXAMPLE 3

3-[2-(Vinyloxy)-ethyl]-5,5-pentamethylene-hydantoin 840.9 g (5.0 mols) of 5,5-pentamethylenehydantoin, 559.3 g (5.0 mols+5% excess) of 2-chloroethyl vinyl ether, 363.4 g (2.5 mols+5% excess) of anhydrous potassium carbonate and 1,500 ml of dimethylformamide are stirred for 4 hours and 5 minutes at 117°–125° C., using the method described in Example 1. The reaction product is filtered hot and the clear filtrate is concentrated on a rotary evaporator at 100° C. under vacuum from a water-pump. After drying to constant weight at 60° C. and 0.5 mm Hg, 1171.2 g (98.0% of theory) of the vinyl ether, melting at 101°–109° C., are obtained.

Elementary analysis: calculated: 60.49% C, 7.62% H, 11.76% N; found: 60.50% C, 7.63% H, 11.99% N.

The H-NMR spectrum agrees with the following structure:

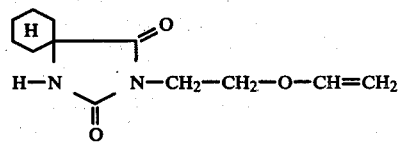

EXAMPLE 4

3-[2-(vinyloxyethyl)]-hydantoin 150.1 g (1.5 mols) of hydantoin, 167.7 g (1.5 mols+2% excess) of chloroethyl vinyl ether, 108.8 g (0.75 mol+5% excess) of anhydrous potassium carbonate and 450 ml of N-methylpyrrolidone are stirred for 3 hours and 30 minutes, using the method described in Example 1. The mixture is then worked up as described in Example 1 and 247.1 g of a crystalline, brown crude product (96.8% of theory) are obtained and are purified by extraction with ether in a Soxhlet apparatus. Yield of pure product: 156.3 g (61.2% of theory). The product melts at 81°–83° C. and gives the following elementary analysis values:

calculated: 49.41% C, 5.92% H, 16.46% N; found: 49.62% C, 5.88% H, 16.64% N.

The H-NMR spectrum agrees with the following structure:

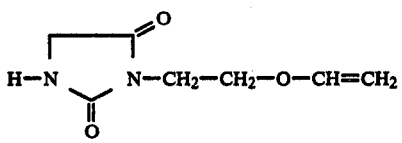

EXAMPLE 5

1-Methyl-3-(2-vinyloxyethyl)-hydantoin

A mixture of 82.6 g (0.72 mol) of 1-methylhydantoin, 50.7 g (0.37 mol) of anhydrous potassium carbonate, 89.6 g (0.84 mol) of 2-chloroethyl vinyl ether, 700 ml of dimethylformamide and 100 ml of toluene is reacted for 2 hours and 30 minutes at 130°–138° C., whilst removing the water of reaction. The mixture is then worked up as described in Example 1, and 128.5 g of a clear, reddish brown, viscous crude product (96.9% of theory) are obtained. The crude product is distilled (boiling point 133° C.–134° C./0.2 mm Hg) and 108.5 g (81.8% of theory) of a colourless, viscous distillate are obtained; this crystallises and melts at 54°–56° C.

Elementary analysis: calculated: 52.17% C, 6.57% H, 15.21% N; found: 51.93% C, 6.69% H, 14.92% N.

The H-NMR spectrum is in accord with the following structure:

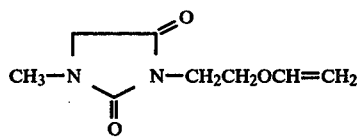

EXAMPLE 6

Bis-[3-(2-vinyloxyethyl)-5,5-dimethyl-hydantoin-1-yl]-methane

A mixture of 134 g (0.5 mol) of bis-(5,5-dimethyl-hydantoin-1-yl)-methane, 106.5 g (1.0 mol) of chloroethyl vinyl ether, 72.6 g (0.5 mol+5% excess) of anhydrous potassium carbonate and 500 ml of dimethylformamide is reacted for 3 hours and 15 minutes at 130°–135° C., analogously to Example 1. The mixture is then worked up as described in Example 1 and 204 g (99.9% of theory) of a light brown crystalline crude product are obtained, and are purified by recrystallisation from methanol. 168.3 g (82.9% of theory) of the pure compound, melting at 90°–92° C., are obtained.

Elementary analysis: calculated: 55.87% C, 6.91% H, 13.72% N: found: 56.04% C, 7.03% H, 13.85% N.

The H-NMR spectrum is in accord with the following structure:

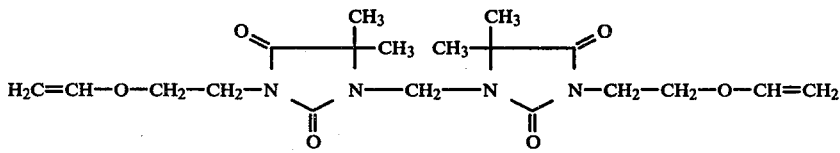

The product may be used, for example, as a component in a formulation for the preparation of partially crosslinked polymers.

EXAMPLE 7

1-Glycidyl-3-(2-vinyloxyethyl)-5,5-dimethylhydantoin 297.3 g (1.5 mols) of 3-(2-vinyloxyethyl)-5,5-dimethylhydantoin, prepared as described in Example 1, 1,387.5 g (15 mols) of epichlorohydrin and 0.5 g of tetramethylammonium chloride are reacted for 2 hours at 107°–115° C. The mixture is cooled to 60° C. and 180 g (1.5 mols+20% excess) of 40% aqueous sodium hydroxide solution are added dropwise in the course of 2 hours, with stirring and whilst removing the water contained in the reaction mixture by azeotropic circulatory distillation. After the addition, distillation is continued for 30 minutes, the mixture is then cooled to room temperature, sodium chloride which has precipitated is filtered off, and the filtrate is concentrated at 80° C. on a rotary evaporator under vacuum from a waterpump. The residue is dried to constant weight at 80° C. and 13.3 Pa and 364.6 g (95.4% of theory) of a brownish, viscous, clear epoxide containing 3.84 equivalents of epoxide/kg (97.8% of theory) are obtained.

The crude product is purified by distillation and 333.5 g (87.4% of theory) of a colourless, clear, viscous distillate boiling at 135° C./5.33 Pa are obtained.

Elementary analysis: calculated: 56.68% C, 7.14% H, 11.02% N; found: 56.7% C, 7.3% H, 11.1% N.

The H-NMR spectrum is in accord with the following structure

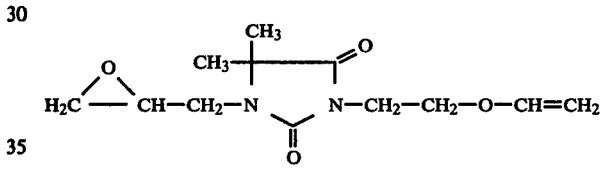

EXAMPLE 8

1-(2-Cyanoethyl)-3-(2-vinyloxyethyl)-5,5-dimethylhydantoin

A mixture of 237.8 g (1.2 mols) of 3-(2-vinyloxyethyl)-5,5-dimethylhydantoin, prepared as described in Example 1, 79.6 g (1.2 mols+20% excess) of acrylonitrile, 0.5 g of hydroquinone, 2.4 ml of a 40% solution of benzyltrimethylammonium hydroxide in methanol and 360 ml of dimethylformamide is allowed to react for 27 hours at 81°–85° C. The solution is then concentrated on a rotary evaporator at 90° C. under vacuum from a waterpump and the residue is dried to constant weight at 90° C. and 13.3 Pa. 300.4 g (99.6% of theory) of a dark brown, crystalline crude product are obtained and are purified by distillation. 260.8 g (86.5% of theory) of a crystalline distillate boiling at 147°–150° C. are obtained. After recrystallisation from ether, the product melts at 54.8°–55.5° C.

Elementary analysis: calculated: 57.36% C, 6.82% H, 16.72% N; found: 57.25% C, 6.84% H, 16.44% N.

The H-NMR spectrum is reconcilable with the following structure:

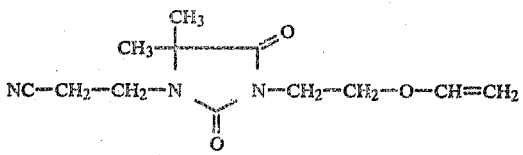

EXAMPLE 9

1-(2-Hydroxypropyl)-3-(2-vinyloxyethyl)-5,5-dimethylhydantoin 297 g (1.5 mols) of 3-(2-vinyloxyethyl)-5,5-dimethylhydantoin, prepared as described in Example 1, 87 g (1.5 mols) of propylene oxide, 7.5 g of lithium chloride and 750 ml of dimethylformamide are allowed to react for 4 hours and 30 minutes at 90°–112° C. A further 83.5 g (1.44 mols) of propylene oxide are then added dropwise in the course of 3 hours and 30 minutes at 112°–113° C. and the mixture is left to react for a further 15 minutes. It is then concentrated on a rotary evaporator at 80° C. under vacuum from a waterpump and dried to constant weight at 80° C. and 13.3 Pa. 382 g (99.6% of theory) of a brown, clear, viscous crude product are obtained and are purified by distillation. 347.7 g (90.4 g) of a clear, colourless distillate boiling at 149°–152° C./13.3 Pa are obtained.

Elementary analysis: calculated: 56.24% C, 7.87% H, 10.93% N; found: 56.22% C, 8.13% H, 10.84% N.

The following structure of the compound is reconcilable with the H-NMR spectrum:

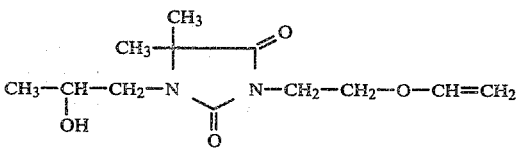

EXAMPLE 10

1-Phenyl-3-(2-vinyloxyethyl)-hydantoin 16.12 g (0.1 mol) of 1-phenylhydantoin, 12.25 g (0.1 mol+15% excess) of 2-chloroethyl vinyl ether, 7.25 g (0.05 mol+5% excess) of potassium carbonate and 50 ml of dimethylformamide are reacted for 1 hour at 120°–125° C. The reaction mixture is worked up analogously to Example 1 and 20.3 g (82.4% of theory) of a brownish, crystalline crude product melting at 119°–120° C. are obtained. 5 g of crude product are recrystallised from 25 ml of chloroform and 3.9 g of the pure compound are isolated. The melting point is 120°–121° C.

Elementary analysis: calculated: 63.40% C, 5.73% H, 11.37% N; found: 63.14% C, 5.75% H, 11.50% N.

The H-NMR spectrum is readily compatible with the following structure:

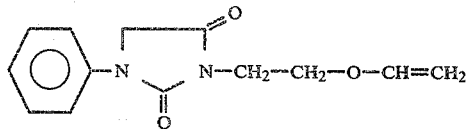

EXAMPLE 11

3-(6-Vinyloxyhexyl)-5,5-pentamethylenehydantoin 4.5 g (0.0267 mol) of 5,5-pentamethylenehydantoin, 5 g (0.0267 mol+15% excess) of 6-chlorohexyl vinyl ether, 2 g (0.0134 mol+5% excess) of potassium carbonate and 15 ml of dimethylformamide are reacted analogously to Example 1. The reaction mixture is then worked up analogously to Example 1 and 7.8 g (99.2% of theory) of a crystalline crude product are obtained, and are purified by distillation in a bulb tube at 190° C. oven temperature and 13.3 Pa. The distillate gives colourless crystals and melts at 82°–83.3° C.

Elementary analysis: calculated: 65.28% C, 8.90% H, 9.52% N; found: 65.16% C, 8.99% H, 9.44% N.

The $^{13}$C-NMR spectrum agrees with the following structure:

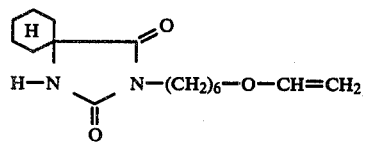

Use examples

I. Homopolymerisation of 3-vinyloxyethyl-5,5-dimethylhydantoin 60 g (0.30 mol) of 3-vinyloxyethyl-5,5-dimethylhydantoin dissolved in 60 ml of benzene are placed in a dry 250 ml round-bottomed flask equipped with a condenser. After having displaced the air in the flask by nitrogen, the benzene solution is warmed to 75° C., and at this temperature 1.0 ml of a 1% BF$_3$ etherate solution in dioxane is added. The exothermic effect is only very slight, with a temperature rise of about 2°–3° C. The solution soon turns cloudy and after 10–15 minutes a yellow mass separates out from the solution, which in the course of 30 minutes becomes distinctly more viscous. When the reaction mixture assumes a dark colour, it is cooled to room temperature.

The benzene is decanted off and the swollen, very sticky polymer is dried in vacuo at 50° C. Yield: 60 g (=100% of theory) of a yellowish brown, stringy, very tacky polymer, which is easily or very easily soluble in acetone, alcohol and dimethylformamide (DMF). Fikentscher K value=8.5 (0.5% solution in DMF at 25° C.). The product may be used, for example, as an adhesive or as a plasticiser for lacquers.

II. (a) Copolymerisation of 3-vinyloxyethyl-5,5-dimethylhydantoin with maleic anhydride (copolymer A)

19.6 g (0.20 mol) of maleic anhydride and 400 ml of benzene are stirred in a 750 ml 4-neck flask equipped with a stirrer, thermometer, condenser and N$_2$ line, at room temperature. Undissolved maleic acid is removed by filtration and the benzene solution is returned to the reaction flask. After displacing the air by nitrogen, a slight stream of nitrogen is passed through the apparatus. 39.6 g (0.20 mol) of vinyloxyethyl-5,5-dimethylhydantoin and 0.5 g of 50% benzoyl peroxide are added to the benzene solution and the batch is stirred briefly. The resulting clear solution is heated to the reflux temperature. After 1½ hours, the paste formed is cooled to room temperature and filtered, and the product is briefly washed with benzene and dried to constant weight in vacuo at 50° C. 56.5 g (=99.5% of theory) of a white powder, carrying a static charge, are obtained.

Anhydride content: 96.5% of theory.

The polymer is insoluble in methyl ethyl ketone, dimethylformamide, tetrahydrofurane and isopropanol.

Instead of a benzene solution, a solution of the reactants in xylene or ethylene chloride could be used. (b) The amide/ammonium salt of copolymer A (compare formula VI)

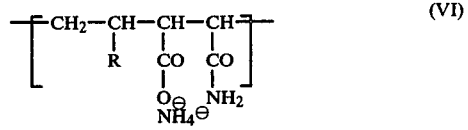

(R=oxyethyl-5,5-dimethyl-hydantoin) may be obtained as follows:

The copolymer of 39.6 g of vinyloxyethyl-5,5-dimethyl-hydantoin and 19.6 g of maleic anhydride, dispersed in 400 ml of benzene, is placed in a 750 ml reaction flask. (Xylene or methylene chloride, for example, could also be used as the dispersing medium). An excess of anhydrous ammonia is passed into the mixture, at room temperature, with thorough stirring, until ammonia escapes through the condenser and the benzene gives a distinctly alkaline reaction (pH 9-10). The mixture is stirred for a further 15 minutes and is then filtered. The filter cake is washed 4 times with 50 ml of benzene, then dried to constant weight in vacuo at 50° C., and ground in a ball mill. The reaction of the copolymer with the ammonia to give the amide/ammonium salt takes place quantitatively. The salt contains structural elements of the formula VI. (c) Both copolymer A and the amide/ammonium salt thereof exhibit a pronounced thickening action which inter alia also depends on the pH value of the liquid to be thickened.

By way of example, copolymer A will be compared with a polyvinylpyrrolidone (PVP) [using LUVISKOL K90, a trademark of BASF] and a copolymer of vinyl methyl ether and maleic anhydride (PVM) [using GANTREZ AN 169, a trademark of GAF].

In each case, 2.5 percent by weight aqueous solutions are prepared and brought to the desired pH value with sodium hydroxide. The viscosity of the solutions is measured with a Brookfield viscometer (model LV, spindle 3, 12 revolutions per minute) at 25° C. At a pH value of 7, the following viscosities are found:

| Copolymer A solution | 2200 cP |
| PVP solution | 110 cP |
| PVM solution | 640 cP. |

Compared to copolymer A, its amide/ammonium salt has certain advantages: it is very easily soluble in water at room temperature without using further additives, such as bases; the aqueous solutions are almost neutral (pH value 6.2); the thickening action is greater; the salt is more free-flowing and does not carry a static charge.

Thickened solutions which are of interest include, for example, those of the following substances in water:
a 15% diammonium sulphate solution for fire-fighting,
a 20% tetrapotassium pyrophosphate solution for cleaners,
a 5% sodium bromate solution for permanent waving formulations,
a 5% sodium hydroxide solution for powerful cleaners, paint removers and the like, and
5% and 10% ammonia solutions for fertilisers.

(d) In aqueous solution, copolymer A exhibits a distinct pseudoplastic behaviour. For a given pH value, the viscosity decreases with increasing speed of revolution of the spindle of the model LV Brookfield viscometer; for example, the following values are measured, using spindle 3, on a 2.5% solution of copolymer A in water in the presence of sodium hydroxide, the pH value being 7:

| Spindle revolutions per minute | 3 | 6 | 12 | 30 | 60 |
|---|---|---|---|---|---|
| Viscosity in cP | 3900 | 2900 | 2150 | 1400 | 1050 |

This pseudoplastic behaviour is technically valuable since it ensures good flow in applications where sher forces arise, as in painting, shampoos and the like. It is particularly advantageous if at the same time there is a thickening action, as is the case with copolymer A and with its amide/ammonium salt. The use of copolymer A or of its amide/ammonium salt in a shampoo results in viscous flow of the shampoo from the bottle, but easy flow, and therefore rapid and uniform distribution through the hair, when the shampoo is worked into the hair.

A comparison with PVP and PVM (compare IIc) shows that though these properties have a similar structure they exhibit no pseudoplastic properties whatsoever. 2.5 percent by weight solutions are prepared and are brought to a pH value of 5.0 with sodium hydroxide solution. The viscosity of the solutions is measured at 25° C. with a model LV Brookfield viscometer, spindle 3, using various speeds of revolution:

| Polymer | Viscosity in cP at the following speeds of revolution (rpm) | | | | |
|---|---|---|---|---|---|
| | 3 | 6 | 12 | 30 | 60 |
| Copolymer A | 6000 | 4000 | 3000 | 1880 | 1250 |
| PVP | 103 | 103 | 104 | 106 | 110 |
| PVM | 3040 | 3260 | 3380 | 3400 | 3400 |

(e) Copolymer A can be used as an anionic, formaldehyde-free dry strength and wet strength agent for paper. The presence of as little as 0.5% of copolymer A in the paper increases the dry tear strength and wet tear strength of the paper to an extent which can only be achieved with larger amounts of known comparable agents, if achievable at all with these. A further advantage of copolymer A is the good shelf of its aqueous solution even at elevated temperatures, for example at the operating temperature of 60° C. used for application in a sizing press in the continuous surface treatment of paper, where the stability of the dry strength and wet strength solutions is important to avoid a decrease in dry strength or wet strength, or to keep such decrease within narrow limits.

Instead of using copolymer A, it is also possible to use its amide/ammonium salt; for example, an 0.9% solution in water is applied to the paper and after pressing-out, the paper is dried at 140° C. so as to leave 1% of dry coating. A substantial increase in dry tear strength and wet tear strength is achieved.

(f) Preparation of the imide 50 g of anhydrous acetic acid and 300 g of acetic anhydride are introduced into a flask and 30 g of the amide/ammonium salt of copolymer A are added, with stirring. An easily stirrable suspension results, which is heated, with stirring. The mixture reaches 95° C. after 45 minutes; the imide which forms dissolves immediately. The reaction mixture is kept at 95°–100° C. for 4 hours. After a reaction time of one hour, a slightly cloudy solution has been obtained, which after a further hour darkens noticeably. At the end of the reaction time of 4 hours, 5 g of active charcoal are added, the mixture is clarified by filtering at 70° C. and the filtrate is then cooled to room temperature.

The clear brown solution is added dropwise in the course of 20 minutes, with thorough stirring, to 1.5 liters of cold water. The product precipitates in a very finely divided form.

After filtration, the filter cake is suspended twice in 500 ml of cold water; finally, the product is washed with cold water until the filtrate is neutral.

After vacuum drying to constant weight at 60°–70° C., a light brown product is obtained, which can be pulverised easily.

Yield: 24.5 g=81.4% of theory. (g) Further salts of copolymer A, for example potassium, ammonium and ethanolamine salts, are prepared by suspending copolymer A in water and adding, with stirring, the amount of the particular base required for dissolving the copolymer.

III. (a) Copolymerisation of 3-vinyloxyethyl-5,5-methylethylhydantoin with maleic anhydride (copolymer B)

21.2 g (0.1 mol) of maleic anhydride are dissolved in 50 ml of dichloropropane and the solution is introduced into a 350 ml 5-neck flask, equipped with a condenser, thermometer, nitrogen line and vacuum line, which already contains 9.8 g (0.1 mol) of vinyloxyethyl-5,5-methylethyl-hydantoin. After brief stirring, a water-clear, colourless solution is produced. The air in the apparatus is displaced by nitrogen and a slight stream of nitrogen is passed in. After adding 0.3 g of 50% benzoyl peroxide, dissolved in 20 ml of dichloropropane, a further 150 ml of dichloropropane are introduced.

The batch is warmed to 60° C. in the course of about 45 minutes, during which a precipitate forms slowly. The temperature is raised to 85° C. in the course of a further 40 minutes and the mixture is stirred for a further 2 hours at this temperature.

It is then cooled to room temperature and the product is filtered off and washed with a small amount of dichloropropane. The resulting product is dried to constant weight in vacuo at 50° C.

Yield: 24.9 g (=80.3% of theory)

The polymer is soluble in methyl ethyl ketone (MEK).

$\eta_{sp}$=0.8625 (measured on a 1% solution in MEK at 25° C.).

K value (by Fikentscher's method)=55.5 (measured on a 1% solution in MEK at 25° C.)

Anhydride content: 95% of theory. (b) This compound can also be converted, by the method described in Example II, into the amide/ammonium salt as well as into other salts, such as Na, K and $NH_4$ salts. (c) The use of copolymer B as a solubilising agent is described below:

The solubility of iodine in water at room temperature is 34 mg/100 ml. It is known that this solubility can be increased by complexing with polyvinylpyrrolidone. 100 ml of a 1% solution of PVP (compare Example IIc) in water will dissolve 580 mg of iodine at room temperature, 100 ml of a 1% aqueous solution of PVM (a copolymer of vinyl methyl ether and maleic anhydride, compare Example IIc) will dissolve 52 mg of iodine, but 100 ml of a 1% aqueous solution of copolymer B of the invention will dissolve about 800 mg of iodine at a pH value of 5.0. The amide/ammonium salt is even capable of dissolving 900 mg of iodine/100 ml.

(d) Esterification of copolymer B:

32.6 g (=0.10 equivalent, based on anhydride groups) of copolymer B are added to a mixture of 14.3 g (=0.11 mol) of 1-octanol and 300 ml of xylene. 2.2 g of di-tert.-butyl-cresol and 2.2 g of p-toluenesulphonic acid are added to the mixture, with stirring, after which the mixture is warmed to 140° C. in the course of 50 minutes and left at this temperature for 24 hours. A brown and somewhat cloudy solution results, which is cooled to room temperature and concentrated to about 250 ml. The ester formed precipitates on adding the solution to 500 ml of n-heptane. After filtering off, and washing with heptane, the slightly tacky filter cake is dried (finally at 120° C. and 2 kPa). 38.4 g of an easily pulverisable ester are obtained. The yield is 89.2%, based on the monoctyl ester.

The diester can be prepared similarly. 3 mols of the alcohol are used per equivalent of anhydride groups of copolymer B.

The following esters were prepared similarly (the degree of esterification being calculated on the basis of the diester):

| Alcohol | Degree of esterification | Description of the product |
|---|---|---|
| 1-Hexanol | 80–85% | yellow to light brown, brittle |
| 1-Dodecanol | 95% | light brown, tough and flexible, slightly tacky, soluble in xylene |
| 1-Octadecanol | 65% | light brown, waxy, soluble in xylene |
| 1-Decanol | 95% | light yellow, brittle, non-tacky, soluble in xylene |
| 1-Decanol | 50% | brown, tough and flexible, slightly tacky, soluble in xylene |

(e) The diesters give attractive clear films, having particularly good mechanical properties, when applied from solvents, such as xylene, and dried at an elevated temperature (for example 160° C.). Attractive, rather soft films having very good resistance to acid can be prepared from the half-ester obtained from 1-octanol, when applied from water after neutralisation with sodium hydroxide solution or with aminomethylpropanol. The films obtained from the half-ester which has been neutralised with sodium hydroxide solution are water-soluble and may be used for packaging, for example, pharmaceutical and cosmetic formulations and agricultural chemicals.

Tacky esters may be used together with zinc oxide, titanium oxide or hydrated aluminium oxide, as bandage adhesives.

Since the degree of esterification is less than 100%, the esters can be crosslinked additionally, for example with polyalcohols, expoxide compounds and the like.

(f) The sodium salt of the monooctyl ester of copolymer B (prepared by adding dilute sodium hydroxide solution to a solution of the monooctyl ester in isopropanol until the pH value is 8-9 and then evaporating the solvent) can be used as a size in the form of an aqueous solution (for example of 16%), can can be applied to olyacrylonitrile fibres and dried at 100° C. The resulting clear, flexible film is distinguished by good adhesion to the fibres, very good water-solubility, and very good removability by washing.

IV. Copolymerisation of 3-vinyloxyethyl-5,5-pentamethylenehydantoin with maleic anhydride (copolymer C)

Using the method described in IIIa, 71.4 g of 3-vinyloxyethyl-5,5-pentamethylenehydantoin (prepared as described in Example 3) and 29.4 g of maleic anhydride are copolymerised by means of 0.9 g of 50% benzoyl peroxide in 500 ml of benzene.

86.8 g of the copolymer (86% of theory) are obtained. The polymer is soluble in DMF.

$\eta_{sp}$=0.3861 (measured on a 1% solution in DMF at 25° C.).

K value (measured by Fikentscher's method)=about 38.5 (measured on a 1% solution in DMF at 25° C.).

This product can also be reacted analogously to II to give the amide/ammonium salt, sodium salt, potassium salt, ammonium salt or the like.

V. Copolymerisation of 3-vinyloxyethyl-hydantoin with maleic anhydride (copolymer D)

25.5 g of 3-vinyloxyethyl-hydantoin (prepared as described in Example 4) are introduced into a 500 ml flask, 14.7 g of maleic anhydride dissolved in 400 ml of benzene are added and the mixture is slowly warmed to 40°-45° C. under a slight stream of nitrogen, whereupon the vinyl ether slowly dissolves. The solution is cooled to 30° C. and 0.35 g of 50% benzoyl peroxide, dissolved in benzene, is added with stirring. The mixture is heated to the reflux temperature of 80° C. in the course of 45 minutes. A thick but easily stirrable paste forms rapidly. The mixture is maintained at the reflux temperature for 2 hours and is then cooled to room temperature and filtered, and the filter cake is washed with a small amount of benzene. The strongly swollen product is dried to constant weight in a vacuum desiccator at 50° C. and 15 mm Hg. The polymer is white and carries a heavy static charge.

Yield: 40.2 g (100% of theory)
Anhydride content: 94.4% of theory.
$\eta_{sp}$=2.7968 (1% solution in DMF at 25° C.)
K value=86.0 (1% solution in DMF at 25° C.)

Derivatives of copolymer D can be prepared, and used, analogously to what has been described under II. The free acid, prepared by saponification at 100° C., can be used as a crosslinking agent for polyfunctional, water-soluble or water-dispersible compounds, such as polyols or polyamines. For example, stoichiometric amounts of butanediol, glycerol or triethylenetetramine are added at room temperature to aqueous solutions of the free acid, and dissolved therein. Films of the resulting 2-component solutions are spread on aluminium sheet by means of a film-spreader frame and are hardened for 10 minutes at 150° C. The films exhibit excellent mechanical properties and very good resistance to organic solvents.

VI. Copolymerisation of 1-methyl-3-vinyloxyethylhydantoin with maleic anhydride (copolymer E)

18.4 g of 1-methyl-3-vinyloxyethyl-hydantoin (prepared as described in Example 5) and 9.8 g of maleic anhydride are copolymerised with 0.25 g of 50% benzoyl peroxide in 250 ml of benzene, analogously to the method described under V. 27.1 g (=96.1% of theory) of a white substance are obtained.

Anhydride content=98.3% of theory.
$\eta_{sp}$=0.2097 (1% solution in DMF at 25° C.)
K value=27.0 (1% solution in DMF at 25° C.).

Derivatives of copolymer E can be prepared, and used, in an analogous manner to that described under II, III and V.

VII. Terpolymerisation of 3-vinyloxyethyl-5,5-dimethylhydantoin with maleic anhydride and styrene (terpolymer E)

9.8 g (0.10 mol) of maleic anhydride are dissolved in 400 ml of benzene. 19.8 g (0.10 mol) of 3-vinyloxyethyl-5,5-dimethyl-hydantoin and 10.4 g (0.10 mol) of destabilised, purifed styrene (washed with 10% NaOH solution and with distilled water, and then distilled in N₂) are added to the benzene solution. 0.3 g of 50% benzoyl peroxide, dissolved in a small amount of benzene, is added to the reaction mixture under nitrogen, after which the mixture is slowly warmed under a stream of nitrogen. After 50 minutes, the temperature has risen to 81° C. the benzene refluxes and the polymer paste formed becomes visibly thicker. After a further 100 minutes at 80°-81° C., the mixture is cooled to room temperature and filtered, and the product is washed with twice 50 ml of benzene. The terpolymer is then dried to constant weight in vacuo at 50° C. and is ground in a ball mill. It is a white, infusible powder. It is insoluble in methanol, chloroform and benzene, but swells in acetone, MEK, DMF, phenol and tetrachloro ethane (1:1).

Yield: (without working up the mother liquor): 27.97 g (70% of theory).

On warming, the product softens, and decomposes at 200° C.

The amide/ammonium salt can be obtained analogously to the method described under IVb. The sodium salt and the amide/ammonium salt show an exceptionally powerful thickening action in water at a pH value of 7:

0.5% by weight of Na salt: 33 Pas; amide/ammonium salt 13.5 Pas

1% by weight of Na salt: 82 Pas; amide/ammonium salt 56 Pas 2.5% by weight of Na salt: 98 Pas; amide/ammonium salt 88 Pas Further salts of the terpolymer A may be prepared as described under IV g).

If instead of styrene 10.0 g of isobutyl vinyl ether are used when preparing the terpolymer, but an analogous method is employed, a white powder carrying a static charge is obtained (without working up the mother liquor) in an amount of 27.5 g (69.4% of theory).

VIII. Terpolymerisation of 3-vinyloxyethyl-5,5-methylethylhydantoin with maleic anhydride and styrene (terpolymer B)

21.2 g (0.10 mol) of 3-vinyloxyethyl-5,5-methylethyl-hydantoin, 10.4 g (0.10 mol) of styrene and 9.8 g (0.10 mol) of maleic anhydride are reacted in 400 ml of benzene, in the presence of 0.3 g of 50% benzoyl peroxide, in the same manner as described under VII. A white powder carrying a static charge is obtained, which softens and decomposes at above 200° C. The powder is insoluble in MEK, chloroform, benzene and acetone, and swellable in methanol, DMF, phenol and tetrachloro ethane (1:1). The swollen particles are transparent.

Yield: (without working up the mother liquor)=28.7 g (69.3% of theory).

This terpolymer can also be used in the same way as that described under VII.

IX. Terpolymerisation of 3-vinyloxyethyl-5,5-pentamethylenehydantoin with maleic anhydride and styrene (terpolymer C)

23.8 g (0.10 mol) of 3-vinyloxyethyl-5,5-pentamethylene-hydantoin, 10.4 g (0.10 mol) of styrene and 9.8 g (0.10 mol) of maleic anhydride in 400 ml of benzene are reacted in the presence of 0.3 g of 50% benzoyl peroxide, in the same manner as described under VII. A white powder which carried a static charge is obtained; it softens on warming and decomposes at above 180° C. It is soluble in acetone, MEK, DMF, phenol and tetrachloro ethane (1:1), and insoluble in methanol, chloroform and benzene.

Yield (without working up the mother liquor)=30.8 g (70.0% of theory).

$\eta_{sp}$=0.2527 (1% solution in MEK)

K value=30.5 (1% solution in MEK).

Derivatives of terpolymer C can be prepared, and used, in an analogous manner to that described for terpolymers A and B. For example, a film is prepared by mixing a solution of 10 g of the amide/ammonium salt of terpolymer C in water with 15.4 g of a 10% aqueous solution of a hydantoin-epoxide resin (epoxide content 7.3 equivalents/kg), and is hardened at 160° C. The film is resistant to chemicals, for example to $H_2O$, $H_2SO_4$, acetone and chlorobenzene.

X. Terpolymerisation of 3-vinyloxyethyl-hydantoin with maleic anhydride and styrene (=terpolymer D)

25.5 g (0.15 mol) of 3-vinyloxyethyl-hydantoin (prepared as described in Example 4), 15.6 g (0.15 mol) of styrene and 14.7 g (0.15 mol) of maleic anhydride are reacted in 450 ml of benzene, in the presence of 0.45 g of 50% benzoyl peroxide, in an analogous manner to that described under IX. A white substance, carrying a static charge, is obtained in an amount of 44.2 g (=79.2% of theory).

$\eta_{sp}$=1.4613 (1% solution in DMF at 25° C.)

K value=69.0 (1% solution in DMF at 25° C.).

The product obtained can be converted to salts in the same way as the terpolymers described earlier, and can be used for similar purposes. For example, the ethanolamine salt of terpolymer D is a highly effective thickener for aqueous systems:

| Concentration of the aqueous solution (pH = 5.2) | Viscosity in Pas |
|---|---|
| 0.25 | 21 |
| 0.5 | 160 |
| 1.0 | 1,650 |
| 2.5 | 1,800 |

XI. Terpolymerisation of 1-methyl-3-vinyloxyethylhydantoin with maleic anhydride and styrene (terpolymer E)

18.4 g (0.1 mol) of 1-methyl-3-vinyloxyethylhydantoin (prepared as described in Example 5), 9.8 g (0.1 mol) of maleic anhydride and 10.4 g (0.1 mol) of styrene are reacted in 300 ml of benzene, in the presence of 0.35 g of 50% benzoyl peroxide, in an analogous manner to that described under VII.

34.2 g (L=88.6% of theory) of a white substance are obtained.

$\eta_{sp}$=0.4452 (1% solution in DMF at 25° C.)

K value=41.0 (1% solution in DMF at 25° C.)

Derivatives of terpolymer E can be prepared, and used, in an analogous manner to that described for the other terpolymers.

Comparative example

(a) 3-Allyl-5,5-dimethylhydantoin 640.6 g (5 mols) of 5,5-dimethylhydantoin, 420.9 g (5 mols+10% excess) of allyl chloride, 380.1 g (2.5 mols+10% excess) of potassium carbonate and 1,000 ml of dimethylformamide are reacted, and worked up, analogously to Example 1. 820 g (97.5% of theory) of a brownish waxy crude product are obtained and are purified by distillation. 713.7 g (84.9% of theory) of a distillate are obtained; this boils at 114° C./13.3 Pas and melts at 66.2°–68.7° C.

Elementary analysis: calculated: 51.13% C, 7.19% H, 16.66% N: found: 56.97% C, 6.98% H, 16.95% N.

The H-NMR spectrum is in good accord with the following structure:

$$\begin{array}{c} CH_3 \\ CH_3 - \overset{|}{\underset{|}{C}} - \overset{O}{\underset{}{C}} \\ H-N \quad N-CH_2-CH=CH_2 \\ \overset{\|}{O} \end{array}$$

(b) Copolymerisation of 3-allyl-5,5-dimethylhydantoin with maleic anhydride 16.8 g (0.10 mol) of 3-allyl-5,5-dimethylhydantoin (analytically pure material), 9.8 g (0.10 mol) of maleic anhydride and 90 ml of ethylene chloride are introduced into a 350 ml flask equipped with a stirrer, thermometer, condenser and $N_2$ line, and are dissolved, with stirring. The apparatus is twice subjected to vacuum, which is in each case released with nitrogen. A slight stream of nitrogen is then passed through the apparatus throughout the duration of the reaction. 0.35 g of 50% benzoyl peroxide, dissolved in 17 ml of ethylene chloride, is added to the mixture and the batch is warmed to 80° C. After 35 minutes at 80° C., the initially clear solution has become dark. A small amount of a flocculent product precipitates. After a further hour's reaction time, only slightly more of this flocculent product has formed. After a total of 3 hours reaction time at 80° C., the mixture is cooled to room temperature and filtered, and the product is dried in vacuo at 50°–55° C.

Yield: 0.65 g (2.4% of theory).

This indicates that virtually no polymer has formed. Accordingly it is not possible to prepare copolymers of 3-allyl-5,5-dimethylhydantoin with maleic anhydride, which can be used as thickeners, solubilising agents, crosslinking agents and the like, whilst such copolymers can be prepared with the novel vinyl ethers of the invention.

What is claimed is:

1. A hydantoin vinyl ether of formula I

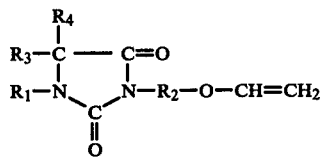

in which $R_1$ is hydrogen, phenyl, methyl, cyanoethyl, glycidyl, hydroxymethyl, hydroxyethyl, hydroxypropyl, acetyl, 2-hydroxy-2-phenyl-ethyl or

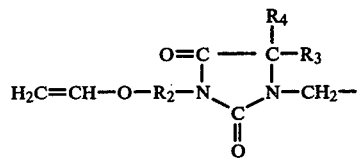

$R_2$ is an alkylene group having 1 to 6 carbon atoms or the $(\text{-alkylene-O-})_n$-alkylene- group, in which the alkylene groups contain 1 to 6 carbon atoms and n is a number from 1 to 6, and $R_3$ and $R_4$ independently of one another are each hydrogen, an alkyl group having 1 to 6 carbon atoms or together are a tetramethylene or pentamethylene group.

2. The hydantoin vinyl ether according to claim 1 which is 3-(2-vinyloxyethyl)-5,5-dimethylhydantoin.

3. The hydantoin vinyl ether according to claim 1 which is 3-(2-vinyloxyethyl)-5-methyl-5-ethylhydantoin.

4. The hydantoin vinyl ether according to claim 1 which is bis-[3-(2-vinyloxyethyl)-5,5-dimethylhydantoin-1-yl]methane.

5. A hydantoin vinyl ether according to claim 1, in which $R_1$ is hydrogen or the methyl group, $R_2$ is the ethylene, propylene or butylene group and $R_3$ and $R_4$ independently of one another are each hydrogen or the methyl, ethyl or isopropyl group, or together are the tetramethylene or pentamethylene group.

* * * * *